(12) United States Patent
Connelly et al.

(10) Patent No.: US 6,750,055 B1
(45) Date of Patent: Jun. 15, 2004

(54) IMPLANTABLE ARTIFICIAL ORGAN AND PHYSIOLOGICAL MONITORING SYSTEM

(75) Inventors: Patrick R. Connelly, Rochester, NY (US); Michael L. Weiner, Webster, NY (US)

(73) Assignee: Biomed Solutions LLC, West Henrietta, NY (US)

( * ) Notice: Subject to any disclaimer, the term of this patent is extended or adjusted under 35 U.S.C. 154(b) by 430 days.

(21) Appl. No.: 09/800,823

(22) Filed: Mar. 7, 2001

(51) Int. Cl.7 .................................................. C12N 5/00
(52) U.S. Cl. ..................... 435/325; 435/283.1; 604/4.01
(58) Field of Search ............................. 435/325, 283.1; 604/4.01

(56) References Cited

U.S. PATENT DOCUMENTS 5,593,673 A * 1/1997 Dinsmore
5,646,035 A * 7/1997 Coon et al.
6,001,647 A * 12/1999 Peck et al.

* cited by examiner

Primary Examiner—Leon B. Lankford, Jr.
(74) Attorney, Agent, or Firm—Howard J. Greenwald

(57) ABSTRACT

An apparatus for regulating the concentration of insulin within the blood of a living organism, wherein said apparatus is comprised of an in vitro cell culture for producing insulin, an in vitro cell culture for producing glucagon, an in vitro cell culture for producing somatostatin, means for measuring the concentration of glucose within the blood of such living organism, means for measuring the concentration of insulin within the blood of such living organism, means for delivering a specified amount of insulin to the blood of such living organism, means for delivering a specified amount of glucagon to the blood of such living organism, means for delivering a specified amount of somatostain to the blood of such living organism, and means for reducing the amount of insulin within such blood of such living organism.

20 Claims, 3 Drawing Sheets

IMPLANTABLE ARTIFICIAL ORGAN AND PHYSIOLOGICAL MONITORING SYSTEM

FIELD OF THE INVENTION

An artificial organ for delivering a chemical within a living body. The organ contains both a cell culture, a means for controlling the cell culture, and a means for delivering one or more chemicals produced by the cell culture.

BACKGROUND OF THE INVENTION

U.S. Pat. No. 6,001,647, of Ammon B. Peck et al., discloses a process for producing insulin in vitro. According to the patentees, the process of this patent may be used to produce insulin within the body of a diabetic patient.

Diabetes is a major public health problem. Diabetics lack the ability of normal human beings of regulating the glucose concentrations within their blood by producing and ceasing the production of insulin, as appropriate.

Insulin is necessary for the sustaining of life. Without its production, blindness may be produced, hyperketosis may be produced, brain cells may be killed, and the vascular system may be damaged. However, the presence of insulin in the blood is a mixed blessing. Too much insulin, a condition known as hyperinsulimia, has been to cause premature aging, arthritis, and cancer.

The process of the Peck et al. Patent produces insulin regardless of whether it is needed by a particular patient. In such process, islet producing stem cells continually produce insulin. When an apparatus embodying the Peck et al. process is incorporated into a living body, the insulin so produced continually permeate into the blood supply; in Example 12 of such patent, the use of a "permeable encapsulant" is disclosed.

As will be apparent, when insulin is continually discharged into a human body, a point will come when it is no longer serving the function of regulating glucose levels in the body, and, at and after this point, the adverse effects of hyperinsulimia will occur. It is not natural, or desirable, for a person to continually have high levels of insulin in his blood.

It is an object of this invention to provide an apparatus capable of homestatically regulating the level of insulin in a living organism.

It is another object of this invention to provide an apparatus for homeostatically regulating various other hormones within a living organism.

SUMMARY OF THE INVENTION

In accordance with this invention, there is provided an apparatus for regulating the concentration of insulin within the blood of a living organism. This apparatus is comprised of a cell culture for producing insulin, means for measuring the concentration of glucose within the blood of such living organism, means for measuring the concentration of insulin within the blood of such living organism, means for delivering a specified amount of insulin the blood of such living organism, and means for reducing the amount of insulin within such blood of such living organism.

BRIEF DESCRIPTION OF THE DRAWINGS

The invention will be described by reference to this specification and the drawings, in which like numerals refer to like elements, and in which.

DESCRIPTION OF THE PREFERRED EMBODIMENT

Figure 1:
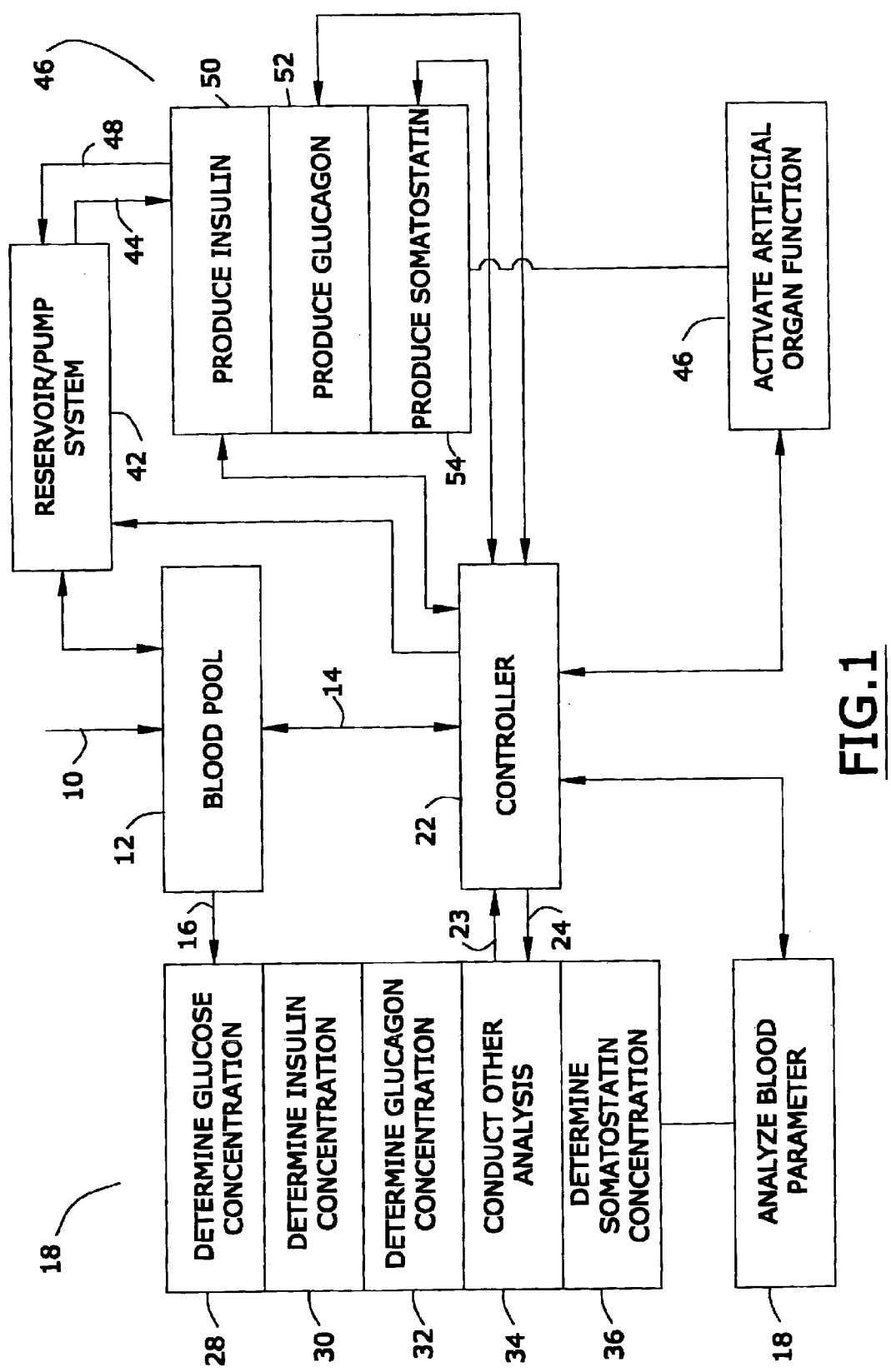
FIG. 1 is a flow diagram of one preferred embodiment of the process of this invention.

FIG. 1 is a flow diagram of one preferred embodiment of the invention. In the first step of the process depicted, the blood of a living organism is fed via line 10 to blood pool 12. Blood may be supplied to blood pool 12 by any one of several means. Thus, e.g., one may withdraw blood from a human body by means of a hypodermic needle; in this case, the process of the invention may be practiced outside the living organism, except to the extent that blood is returned to the organism via line 14. Thus, e.g., one may implant a device, such as the device depicted in FIG. 2, within the living organism and collect blood from such organism within an in vivo reservoir; in this case, the process of the invention may be practiced entirely in the such body. Thus, e.g., one may sample blood by one or more of the procedures and devices described in U.S. Pat. No. 6,159,164 (blood supply system), U.S. Pat. Nos. 5,902,253, 5,759,160 (hybrid portal), U.S. Pat. Nos. 5,387,192, 4,871,351 (implantable medication infusing system), U.S. Pat. No. 4,832,034, and the like; the entire disclosure of each of these United States patents is hereby incorporated by reference into this specification.

Referring again to FIG. 1, a portion of the blood in the blood pool 12 is fed via line 16 to anaylzer 18. In analyzer 18, one or more blood parameters may be analyzed in response to a signal from controller 22 fed via line 24. The information obtained by such analyses is returned to the controller 22 which, in response to such information, may activate an artificial organ function and/or may take or cause to be taken one or more other actions.

In one embodiment, illustrated in FIG. 1, the controller 22 causes the analyzer 18 to determine the concentration of glucose within the blood sample; this is done in step 28. The analysis of the glucose concentration in the blood may be conducted by conventional means such as, e.g., by a glucose sensor assembly. By way of illustration and not limitation, one may use the processes and devices described in U.S. Pat. No. 5,660,163 (implantable glucose monitoring system comprised of a glucose sensor inserted into a patient's venous system), U.S. Pat. No. 5,448,992 (non-invasive phase sensitive measurement of blood glucose concentration), U.S. Pat. No. 5,995,860 (implantable device for sensing in vivo the level of a blood constituent), U.S. Pat. No. 6,175,752 (in vivo monitoring of glucose), U.S. Pat. No. 6,162,611 (subcutaneous glucose electrode), U.S. Pat. No. 6,143,164 (in vitro glucose sensor), and the like. The disclosure of each of these United States patents is hereby incorporated by reference into this specification.

In step 30 of the process depicted in FIG. 1, the insulin concentration of the blood sample is determined. In step 32 of the process, the glucagon concentration of the blood sample is determined. The determinations may be made in accordance with prior art procedures and devices. Thus, e.g., one may use one or more of the procedures and devices described, e.g., in U.S. Pat. Nos. 4,792,597, 5,070,025, 6,180,336, 6,002,000 (chemiluminscent compound and method of use), U.S. Pat. No. 5,9365,070, and the like. The disclosure of each of these United States patents is hereby incorporated by reference into this specification.

Referring again to FIG. 1, other analysis or analyses may optionally be conducted in step 34 of the process. Thus, by way of illustration and not limitation, one can analyze the expression of certain blood factors which are known or believed to cause disease. In step 36 of the process, which is optional, the concentration of somatostatin is determined.

As is known to those skilled in the art, somatostain inhibits the secretion of both insulin and glucagon, as well as growth hormone and thyroid-stimulating hormone. See, e.g., page 765 of John B. West's "Best and Taylor's Physiological Basis of Medial Practice," Twelfth Edition (Williams and Wilkins, Baltimore, Md., 1991). Reference may also be had to U.S. Pat. Nos. 6,011,008, 5,531,925, 5,491,131, 5,260,275, and the like. The disclosure of each of these United States patents is hereby incorporated by reference into this specification.

As will be apparent to those skilled in the art, for proper homestatic regulation of glucose and insulin within a living organism, glucose, insulin, glucagon, and somatstatin all must be present in specified concentrations and ratios. The process of this invention allows one to produce the conditions necessary for ideal homeostatic regulation of such analytes.

The information produced in analyzer 18 is fed to controller 22 via line 23, which produces a computer-readable profile representing the identity and relative abundance of the glucose, insulin, glucagon, and somatostatin in the blood. The controller is equipped with an algorithm which it can determine the ideal concentration of each such analyte and can thereafter cause additional insulin and/or glucagon and/or somatostatin and/or other analyte to be added to the blood pool 12.

Controllers for analyzing and regulating the composition of a biological fluid are known. Thus, e.g., in U.S. Pat. No. 6,064,754, computer-assisted methods and devices for identifying, selecting, and characterizing biomolecules in a biological sample are disclosed. Thus, for example, one may use one or more of the processes or devices described in U.S. Pat. Nos. 6,185,455, 6,122,536 (implantable sensor for measurement and control of blood constituent levels), U.S. Pat. Nos. 5,995,960, 5,978,713, 5,971,931, 5,967,986, and the like. The disclosure of each of these United States patents is hereby incorporated by reference into this specification.

In one embodiment, the controller contains a processing system utilizing an application specific integrated circuit ("ASIC"). These ASIC controllers are well known and are described, e.g., in U.S. Pat. Nos. 5,937,202, 6,041,257, 6,165,155, and the like. The entire disclosure of each of these United States patents is hereby incorporated by reference into this specification.

In one embodiment, the controller comprises a processor complex for processing data fromat least one input, comprising at least a first and second processor, each having a data input and a data output, a data input of the second processor receiving data from the data output of the first processor; each processor being programmed with a respective algorithm for processing data received from a respective data input; said first processor being configured to receive raw data and process the raw data according to the respective algorithm programmed therein, and configured to receive other raw data and pass said other raw data to said second processor; and said second processor being configured to receive said other raw data passed from said first processor and process the other raw data according to the algorithm programmed in said second processor, and said second processor is configured to receive processed data from said first processor and pass the processed data from the data input to the data output of said second processor.

Based upon the analyses of the analytes found in the blood sample, the controller 22 will cause either insulin and/or glucagon and/or somatostatin to be withdrawn from blood pool 12 via reservoir/pump system 42 and fed via line 44 to cell culture assembly 46 cell culture assembly 46. Alternatively, or additionally, reservoir/pump system 42 can pumpinsulin-containing material and/or glucagon-containing material and/or somatostatin-containing material via line 48 and send it to blood pool 12. The reservoir/pump system is equipped with various filtration and separation devices so that it is capable of separating the insulin and/or glucagon and/or somatostatin from blood with which it may be admixed and returning the blood so separated to blood pool 12.

In another embodiment, the reservoir/pump system 42 is comprised of an insulin pump. Such insulin pumps are well known to those skilled in the art and are described, e.g., in U.S. Pat. Nos. 6,181,957, 6,168,575, 6,165,155, 6,162,611, 6,135,978, 6,124,134, 6,123,668, and the like. The entire disclosure of each of these United States patents is hereby incorporated by reference into this specification.

In yet another embodiment, the reservoir/pump system is comprised of a pump for pumping or withdrawing analytes such as insulin, glucagon, and somatostatin. One may use for this purpose conventional implantable drug delivery devices. Thus, by way of illustration and not limitation, one may use the devices disclosed in U.S. Pat. No. 5,836,985 (a refillable, rate-controlled drug delivery device with a hollow reservoir), U.S. Pat. No. 5,607,418 (implantable drug delivery apparatus), and the like. Regardless of the device used, the analyte is added to or withdrawn from the blood pool as dictated by the analyses performed by the controller 22.

Reservoirs 46 includes a reservoir 50 in which a tissue culture produces and accumulates insulin. Tissue cultures which produce insulin are well known.

As is known to those skilled in the art, one can grow embryonic Islet of Langerhan cells /w/ Acinar cells of the pancreas in vitro. These form a pseudo organ that can produce insulin. Murine embryonic pancreata can be dissected under a microscope. Different conditions can be applied to culture these samples to form, which will differentiate into functional in vitro pancreata.

Reference may be had to U.S. Pat. No. 6,110,743 (the creation of genetically engineered cells and their use in transplant therapy. The entire disclosure of this United States patent is hereby incorporated by reference into this specification.

Reference may also be had to U.S. Pat. No. RE036,844 (cellular attachment to trans-epithelial Appliances. Method of forming three-dimensional epithelial cellular structures with components normally derived in developing organs, and the use of 804G cells [rat bladder carcinoma cells] for the production of hemi-desmosome components that are responsible for attachment of epithelial cells to the basement membrane). In a preferred embodiment an implantable device that is a biocompatible object (ie. Stainless steel mesh) which can be molded to any shape. The material is coated with the soluble factor from 804G cells responsible for producing ectopic hemi-desmosome formation through the attachment of any number of cells. Epithelial cell interaction with the basement membrane is a strict requirement for proper functionality of a variety of epithelial and mesenchymal cell types.

Referring again to FIG. 1, and in the preferred embodiment depicted therein, glucagon is produced by a cell culture in reservoir 52. One may produce glucagon in a cell culture, and/or another hormone in a cell culture 54 (somatostatin) by a process which comprises culturing pancreatic cells from a mammalian species in a basal nutrient medium supplemented with normal serum at below about 0.5% and glucose at below about 1 millimolar, allowing said insulin producing stem cells to grow for at least about 3 weeks, and initiating cellular differentiation into mature islet cells by re-feeding the insulin producing stem cells in culture with a nutrient medium supplemented with normal serum at about 0.5–10% and glucose at about 2.5 to about 10 millimolar; see, e.g., U.S. Pat. No. 6,001,647, the entire disclosure of which is hereby incorporated by reference into this specification.

A Preferred Artificial Organ

Figure 2:
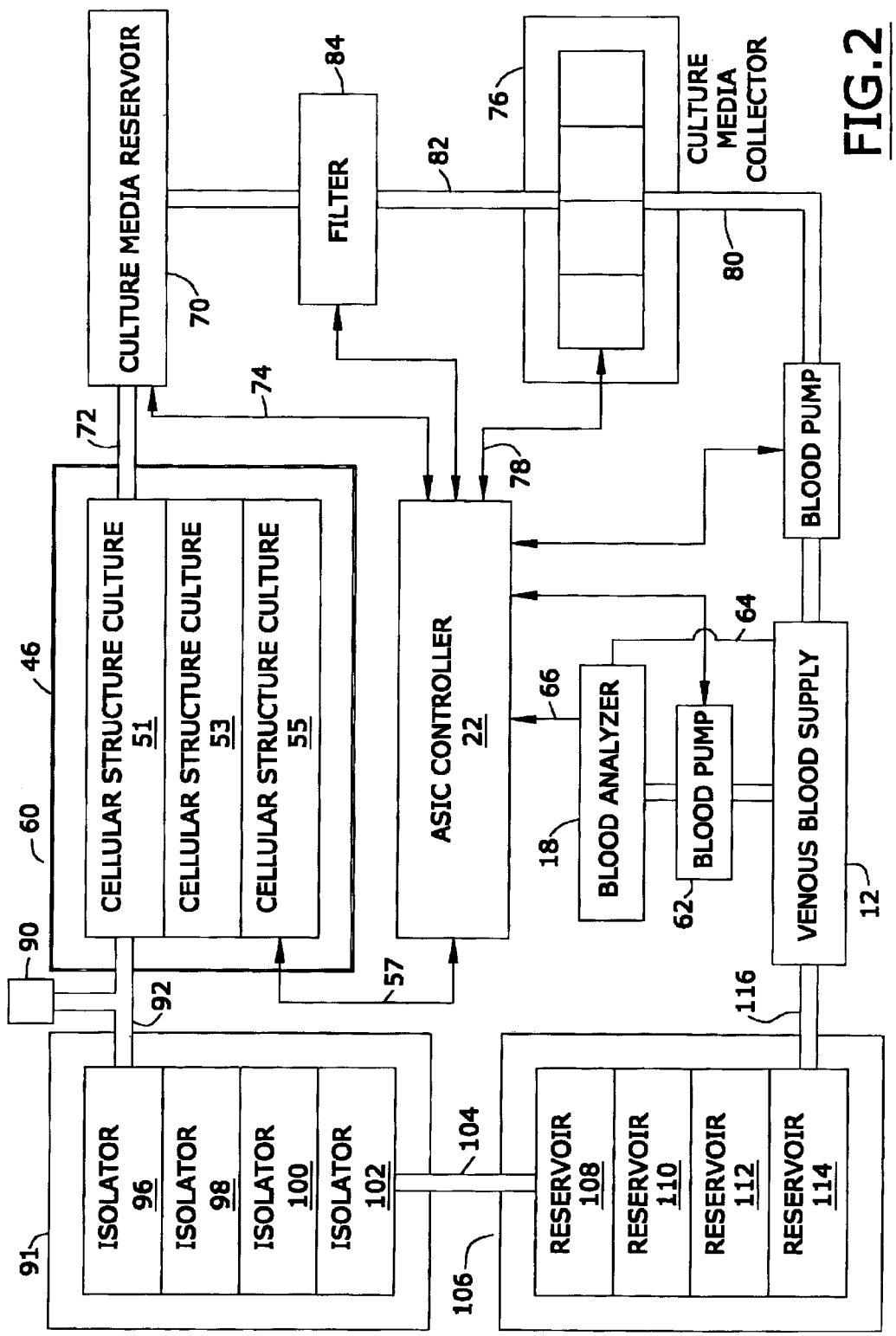
FIG. 2 is a schematic representation of one preferred assembly of this invention.

FIG. 2 is a schematic diagram of one preferred artificial organ 60 which, preferably, is implantable within a living organism. Referring to FIG. 2, a source of venous blood 12 is supplied to the organ 60. The blood may be supplied from a source external to the body, such as via a blood transfusion. In one preferred embodiment, the blood is supplied by a living human body.

Means for withdrawing or segregating or channeling blood from a living organism are well known and are described in, e.g., U.S. Pat. No. 5,902,336 (an implantable device and method for removing fluids from the blood of a patient; this patent presents is a novel approach for the surgical implantation of a filtering device using filters of specified pore size and with the passage of specified flow rates.

By way of further illustration, U.S. Pat. No. 6,123,861 discloses the fabrication of miniaturized drug delivery systems using similar fabrication processes as those used in integrated circuit (IC) production. The devices disclosed in this patent may be used in conjunction with a source of venous blood to supply analytes (such as drugs, hormones, blood constituents, mixtures thereof, etc.) to a system.

A major hurdle in the development of artificial organ systems or in transplant therapy regimes is in the host immune response. Attempts have been made to implant in vitro organ cultures in various anatomical regions of the body in an attempt to replace loss of physiologic function.

By way of further illustration, U.S. Pat. No. 6,001,647 discloses in vitro culture systems, which are manipulated (with, e.g., recombinant genetic techniques) to produce functional Islets of Langerhans. The implantable in vitro systems discussed in this U.S. Pat. No. 6,001,647, and the entire disclosure of this patent are hereby incorporated by reference into this specification. This in vitro culture system of this patent may be used as the precursor for the implantable in vitro capsule described herein. This is only one example of organ type which can to be utilized for the present invention. Additional organ and cellular structures may require much different culture conditions.

Referring again to FIG. 2, and in the preferred embodiment depicted therein, blood is withdrawn via a catheter (not shown) from venous blood supply 12 to blood analyzer 18 via pump 62. After such blood is analyzed, it is returned is returned to blood supply 12 via line 64. In one embodiment, this process is continuous.

The information obtained from the blood analyses is fed via communications line 66 to ASIC controller 22. In one embodiment, in addition to analyzing the hormone levels in the venous blood supply 12, and controlling the amount of analyte released from reservoir 46 (see FIG. 1), the controller 22 preferably controls the type and concentrations of constituents fed into the cell culture system 46 which are necessary for the in vitro production of the desired analytes. These reagents are fed a culture media reservoir 70 which feeds these reagents via line 72 to cell culture assembly 46 in response to signals from controller 22 fed back and forth via line 74.

The reagents which are fed from culture media reservoir 70 are initially collected in culture media collector. The controller 22 furnishes information to collector 76 via line 78 as to the type and concentration of the various analytes which are required for the maintenance of the in vitro cell culture system 46. These analytes are initially fed to collector 76 via line 80 and, thereafter, it is passed via line 82 to filter 84, in which the analytes are sterilized and purified.

As is known to those in the art of cell culturing, the filter removes bacteria, immunogens, and other agents which are not conducive for the desired in vitro cell culture processes.

In one embodiment, the pH of the material in the cell culture reservoir 70 is monitored to insure that it preferably is between 7.1 to 7.4. If the pH measured in reservoir 70 is lower than this range, controller 22 signal culture media collector 76 to extract carbonic anhydrase (carbonic acid minus a hydrogen ion) from venous blood supply 12 to feed it to filter 84 and thence to culture media reservoir 70, where its presence will increase the pH. Conversely, if the pH in reservoir 70 is higher than the desired range, carbonic anhydrase may be withdrawn from the reservoir 70.

In a similar manner, the pH within the cell culture assembly 46, and within each of the compartments 51, 53, and 55 thereof, may also be adjusted by the addition or removal of the carbonic anhydrase, in response to signals from the controller 22 (see line 57). In this embodiment, the carbonic anhydrase may be fed via line 72 to cell culture assembly 46 and/or any component thereof.

As will be apparent, there be several information streams fed into the controller 22, including streams of the information about the pH in both reservoir 70 and cell culture assembly 46. The controller 22 evaluates all of these factors and then determines precisely what mix of reagents is needed to feed via lines 80, 82, and 72 to obtain the desired pH range (and anayltes) in both culture reservoir 70 and cell culture assembly 46. In addition to the carbonic anhydrase, the controller 22 may cause the feed other other pH-modifying analytes to adjust the pH.

Referring again to FIG. 2, the analytes required by the body to maintain the desired homeostasis condition(s) are withdrawn, as needed, from cell culture assembly 46 by pump 90 and fed vial line 92 to isolator assembly 94.

Isolator assembly 94 is comprised of a multiplicity of isolation filter columns 96, 98, 100 and 102, which, by appropriate purification and elution techniques, isolate one or more purified for each of columns 96, 98, 100, and 102 et seq. The purified analytes are then fed, as needed, via line 104 to reservoir assembly 106, in which one or more of the purified analytes may be separately stored in reservoir chambers 108, 110, 112, 114 et seq. Based upon the directions received from controller 22, these purified analytes maybe fed into venous blood supply 12 via line 116.

In one embodiment, the analyte(s) in each of reservoir chambers 108, 110, 112, and 114 are diluted in a separate dilution chamber (not shown) disposed within each such reservoir. It is preferred that the analyte(s) be diluted with blood plasma, which contains neither red blood cells nor white blood cells.

Figure 3:
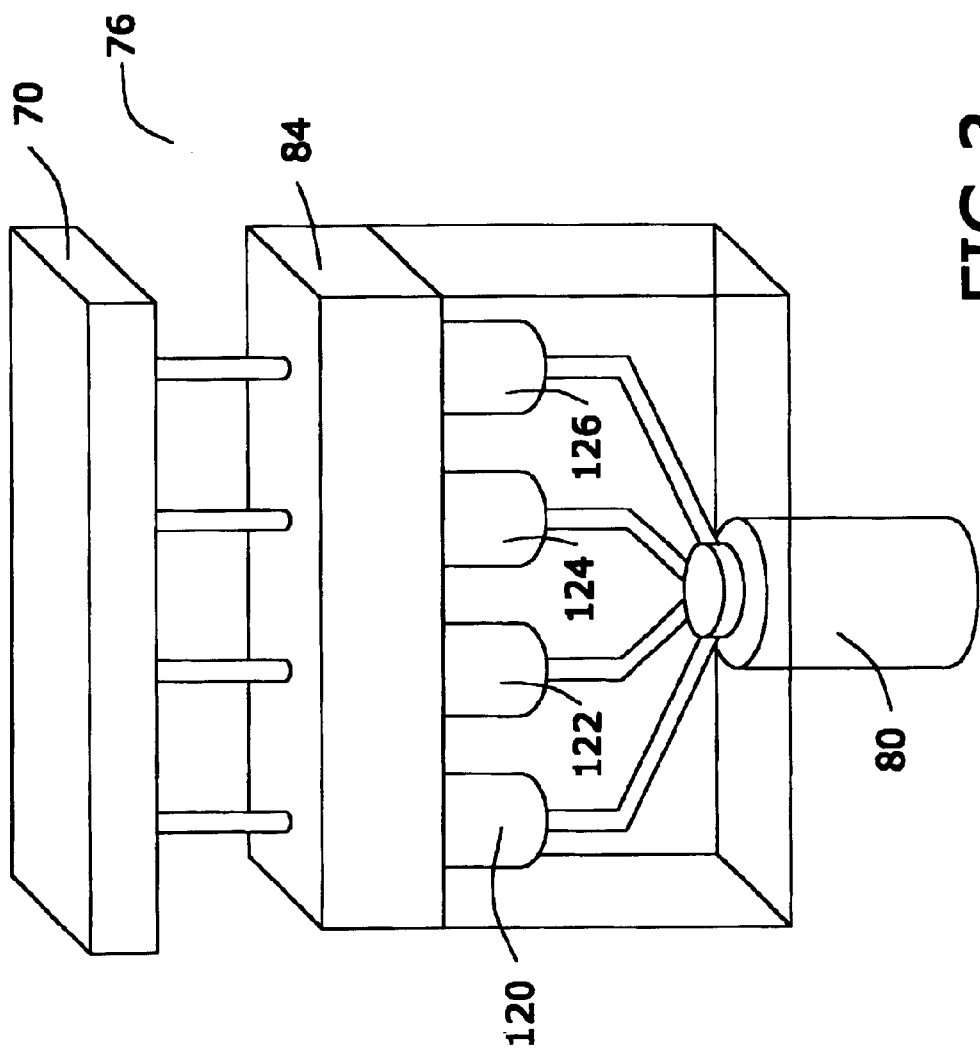
FIG. 3 is a schematic representation of another preferred assembly of this invention.

FIG. 3 is schematic view of a preferred embodiment of culture media collector 76. Referring to FIG. 3, it will be seen that collector 76 is comprised of input port 80 which communicates with filter banks 120, 122, 124, and 126. Although only four such filter banks, and associated lines, are illustrated in FIG. 3, it will be apparent that many more (or fewer) filter banks can be used, depending upon the number of analytes involved.

In one embodoiment, the filter banks 120 et seq. are immunoisolation chambers or columns. In another embodiment, one or more of the purification techniques disclosed in Terry M. Phillips et al.'s "Affinity and Immunoaffinity" (Eaton Publishing, 2000) may be used.

The purified outputs from banks 120 et seq. are then fed to filter 84 and thence to culture media reservoir 70.

The device 76, in addition to being used as culture media collector 76, may also be used as the isolator bank 91 and/or as a component of the blood analyzer 18.

The processes and devices disclosed in this specification may be used with a multiplicity of different organ systems. Thus, by way of illustration, it may be used as an implantable dialysis device in the manner discussed in U.S. Pat. No. 5,902,336. Thus, e.g., it may be used as an implantable liver, an implantable bladder (see U.S. Pat. No. 4,961,747), an implantable thymus, an implantable adrenal medulla, and like. By way of further illustration, the devices and processes of this application may be used for the enhancement of T-cell production in immune disorders, for the enhancement of Hepatic function for various liver, disorders, for the enhancement of renal function for various kidney disorders, for the enhancement of digestive function in any number of digestive system disorders, for the enhancement of reproductive function in any number of reproductive system disorders, for the for the enhancement of cardiac function in any number of cardiac disorders, etc.

In one embodiment, the artificial organ of this invention is hermetically sealed entirely to prevent corrosion. It preferred to seal the artificial organ with a biocompatible coating. In an additional embodiment, the enclosed invention may also be used for the early stage detection of tumorigenic and/or metastatic conditions.

In yet another embodiment of this invention the detection of the reduction in specific enzymes required for an efficient and homeostatic physiological condition. Enzymes which are responsible for and/or a product of any and all combinations of efficient physiological function.

It is to be understood that the aforementioned description is illustrative only and that changes can be made in the apparatus, in the ingredients and their proportions, and in the sequence of combinations and process steps, as well as in other aspects of the invention discussed herein, without departing from the scope of the invention as defined in the followings claims.

We claim:

1. An apparatus for regulating the concentration of insulin within blood, wherein said apparatus is comprised of
   an in vitro cell culture for producing insulin,
   an in vitro cell culture for producing glucagon,
   an in vitro cell culture for producing somatostatin,
   means for measuring the concentration of glucose within said blood,
   means for measuring the concentration of insulin within said blood,
   means for delivering a specified amount of insulin to said blood,
   means for delivering a specified amount of glucagon to said blood,
   means for delivering a specified amount of somatostatin to said blood,
   and means for reducing the amount of insulin within said blood, wherein:
   (a) said means for measuring the concentration of glucose within said blood and said means for measuring the concentration of insulin within said blood and said means for measuring the concentration of somatostatin within said blood are each connected to an in vitro cell culture wherein
      said in vitro cell culture is selected from the group consisting of
         said in vitro cell culture for producing insulin,
         said in vitro cell culture for producing glucagon,
         said in vitro cell culture for producing somatostatin,
         and combinations thereof; and
   (b) said means for delivering a specified amount of insulin, said means for delivering a specified amount of glucagon, and said means for delivering a specified amount somatostatin each are connected to a measurement means selected from the group consisting of
      means for measuring the concentration of glucose within said blood,
      means for measuring the concentration of insulin within said blood,
      means for measuring the concentration of somatostatin within said blood,
      and combinations thereof.

2. The apparatus as recited in claim 1, wherein said apparatus further comprises means for withdrawing blood from a venous blood supply.

3. The apparatus as recited in claim 2, wherein said apparatus comprises means for detecting the presence of analytes in said venous blood supply.

4. The apparatus as recited in claim 3, wherein said apparatus is comprised of a controller comprised of means for determining the concentration of said analytes in said venous blood supply.

5. The apparatus as recited in claim 2, wherein said apparatus is comprised of means for reducing the amount of glucagon in said venous blood supply.

6. The apparatus as recited in claim 1, wherein said apparatus is comprised of means for reducing the pH of said blood.

7. The apparatus as recited in claim 1, wherein said apparatus is comprised of means for increasing the pH of said blood.

8. The apparatus as recited in claim 3, wherein said apparatus is comprised of means for isolating analytes from said venous blood supply.

9. The apparatus as recited in claim 4, wherein said controller is an application specific integrated circuit controller.

10. The apparatus as recited in claim 1, wherein said apparatus is comprised of a cell culture assembly for producing analyte.

11. The apparatus as recited in claim 10, wherein said apparatus is comprised of a reservoir for storing said analyte.

12. The apparatus as recited in claim 11, wherein said apparatus is comprised of a first pump.

13. The apparatus as recited in claim 12, wherein said apparatus is comprised of a blood analyzer.

14. The apparatus as recited in claim 13, wherein said first pump withdraws said blood from said venous blood supply and conveys said blood to a blood analyzer.

15. The apparatus as recited in claim 14, wherein said apparatus is comprised of a second pump.

16. The apparatus as recited in claim 15, wherein said apparatus is comprised of a culture media reservoir.

17. The apparatus as recited in claim 16, wherein said second pump withdraws said blood from said venous blood supply and conveys said blood to said culture media reservoir.

18. The apparatus as recited in claim 17, wherein said apparatus is comprised of an isolator.

19. The apparatus as recited in claim 18, wherein said apparatus is comprised of a third pump for extracting said analyte from said culture media reservoir and conveying said analyte to said isolator.

20. The apparatus as recited in claim 1, wherein said apparatus comprises a filter for purifying and isolating analytes.

* * * * *